United States Patent [19]
Lēhmann et al.

[11] Patent Number: 5,644,011
[45] Date of Patent: Jul. 1, 1997

[54] COATING AND BINDER FOR PHARMACEUTICAL AGENTS

[75] Inventors: Klaus Lēhmann; Thomas Süfke, both of Rossdorf, Germany

[73] Assignee: Roehm GmbH Chemical Factory, Darmstadt, Germany

[21] Appl. No.: 519,357

[22] Filed: Aug. 25, 1995

[30] Foreign Application Priority Data

Aug. 31, 1994 [DE] Germany .................... 9414066 U

[51] Int. Cl.$^6$ .................... C08L 33/02; C08L 33/04; C08L 33/08; C08L 33/12
[52] U.S. Cl. .................... 526/319; 526/317.1; 526/328; 526/328.5; 526/329.7
[58] Field of Search .................... 526/319, 317.1, 526/328, 328.5, 329.7

[56] References Cited

U.S. PATENT DOCUMENTS

| | | | |
|---|---|---|---|
| 4,692,396 | 9/1987 | Uchida | 430/284 |
| 4,729,190 | 3/1988 | Lee | 47/57.6 |
| 5,070,164 | 12/1991 | Min et al. | 526/286 |
| 5,431,920 | 7/1995 | Bechard | 424/480 |

*Primary Examiner*—W. Robinson H. Clark
*Attorney, Agent, or Firm*—Oblon, Spivak, McClelland, Maier & Neustadt, P.C.

[57] ABSTRACT

Coatings and binders for pharmaceutical forms containing a copolymerizate, wherein the copolymerizate is made up of:

A) 10 to 25 wt % methacrylic acid;
B) 40 to 70 wt % methyl acrylate; and
C) 20 to 40 wt % methyl methacrylate; based on the total weight of the copolymerizate.

20 Claims, 1 Drawing Sheet

COATING AND BINDER FOR PHARMACEUTICAL AGENTS

BACKGROUND OF THE INVENTION

1. Field of the Invention

The present invention relates to coatings and binders for pharmaceutical forms which contain a copolymerizate of ethylenic, unsaturated, radical and polymerizable monomers with a carboxyl group and alkyl esters of such monomers which are present, preferably as latex dispersed in an aqueous phase, as well as to the use of the coatings and binders and the pharmaceutical forms produced with them.

2. Description of the Background

From DE-C 2,135,073, coatings for pharmaceutical forms are known in the form of an aqueous dispersion. These coatings contain emulsion polymerizates which, in general, are made up of 50 wt % methyacrylic acid and 50 wt % methyl or ethyl acrylate. A binder of this type is known in commerce under the trade name, EUDGRAGIT L30D (trademark of Röhm GmbH, Darmstadt).

Drug coatings produced from this binder are insoluble in the acid milieu of the gastric juice, and dissolve in gastric juice only at a pH value of 5.5 and more, and then release the core containing the active ingredient for dissolution. For different active ingredients, different release characteristics are desirable. Some pharmaceutical forms are intended to release the active ingredient immediately after entry of the pharmaceutical form into the duodenum or the upper intestinal section at pH values of approximately 5 to 6, while others do not do so until entering the lower intestinal areas, as far as the colon, at pH values of approximately 6 to 7.5. For this reason, a sufficiently broad palette of coating agents is desired for different release pH values in order to control the release of the active ingredient in these sections of the intestine.

The release characteristics of drug coatings in vitro are tested according to USP, normally with artificial gastric juice (0.1N HCl) and artificial intestinal juice (pH 6.8). In order to determine the gradual dissolution in the intestinal region, it has proven expedient to determine the release rate of a water-soluble substance from the pharmaceutical form first within 2 h in artificial gastric juice, and then in buffer solutions, and, beginning at pH 5.0, to change the buffer solution every 60 min, whereby the pH value is gradually increased by 0.5 in each case.

From EP-B 152,038, aqueous coating agents are also known which also allow the production of pharmaceutical forms with a release pH of value of 7 to 7.5. However, this requires the mixing of at least two coating dispersions, of which one is responsible for pH control and the other for the adjustment of elasticity. This neutral polymerizate component is, however, insoluble in the gastric juice and frequently causes an undesirable delay of dissolution even after the desired pH value has been reached.

Thus, a need exists for a coating agent which can be used in the form of an aqueous dispersion and which dissolves in the deeper areas of the intestine or colon, and which allows release of the coated active ingredient when an acceptable pH level is reached.

SUMMARY OF THE INVENTION

Accordingly, one object of the invention is to provide a coating agent which can be used in the form of an aqueous dispersion and which supplies coatings which dissolve in the deeper sections of the intestine or in the colon and which allow release of the active ingredient only when an acceptable pH level is reached.

The above objects and other are provided by a coating and/or binder for pharmaceutical forms, containing a copolymerizate, which is made of:

A) about 10 to 25 wt % of methacrylic acid,

B) about 40 to 70 wt % of methyl acrylate,

C) about 20 to 40 wt % of methyl methacrylate, based on a total copolymerizate weight of 100 wt. %.

DETAILED DESCRIPTION OF THE PREFERRED EMBODIMENTS

Figure 1:
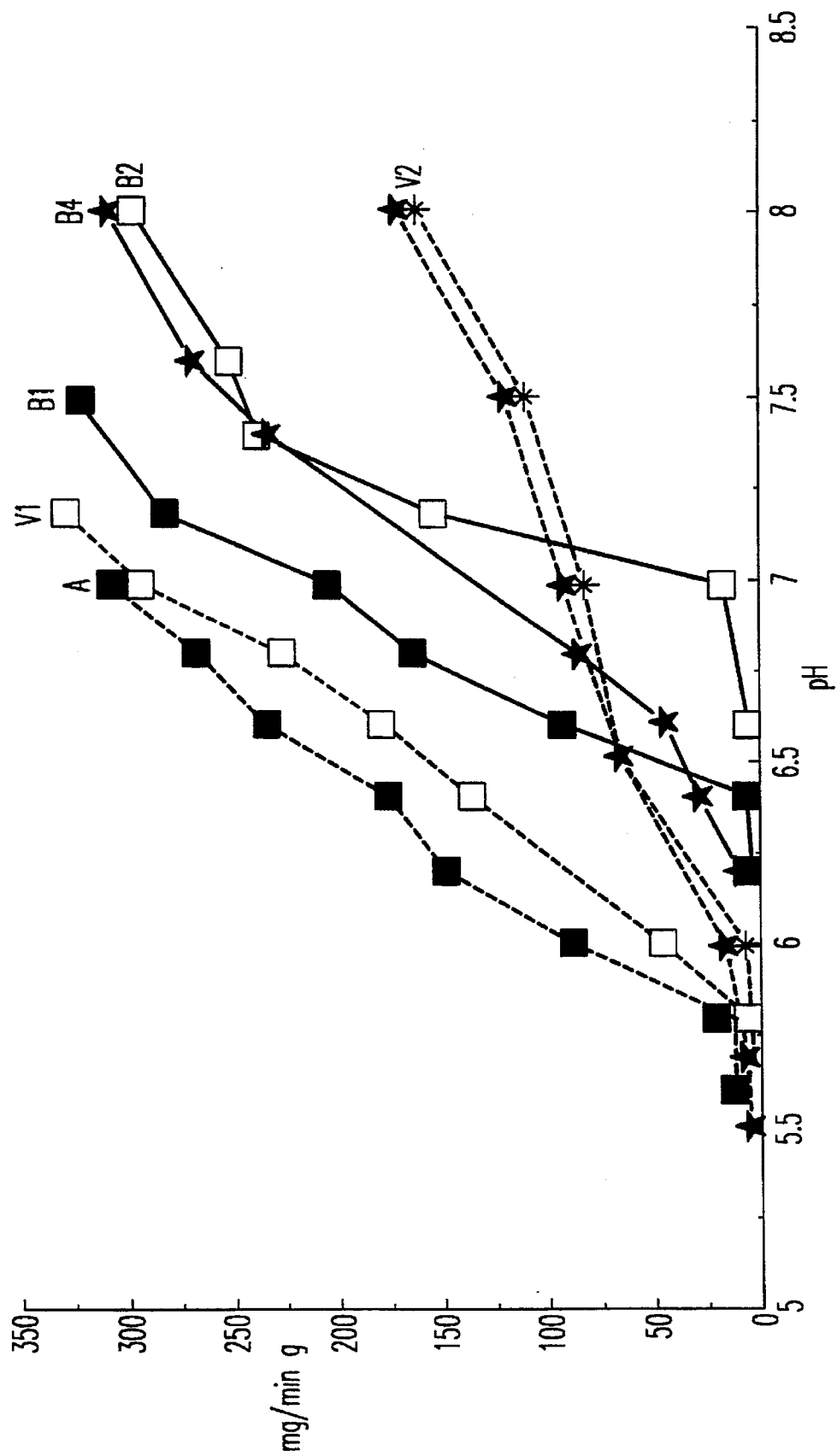
FIG. 1 illustrates the dissolution characteristics of the present coating as compared to other coating agents.

In accordance with the present invention, a coating agent is provided which can be used in the form of an aqueous dispersion and which provides coatings which dissolve in the deeper section of the intestine and in the colon and which allows release of the active ingredient from the coated pharmaceutical forms beginning only with a pH of about 6.5 to 7.0 in the test method given above, and which allows a release at a pH of at most 7.5 from 120 min. However, the advantageous application properties of the known aqueous coating agents must be maintained. Therefore, formation of the film should take place below 30° C. during drying of the coating which contains not more than 10 wt % softener relative to the emulsion polymerizate.

In fact, the proposed objective of the present invention cannot be resolved starting with a common commercial coating agent on the basis of a copolymerizate of methacrylic acid and ethyl acrylate in a ratio of 50:50, and then merely reducing the methacrylic acid portion in the copolymerizate. In so doing, only a temporary delay of dissolution is achieved, that is, a flatter course of the release curve is obtained, however, an increase of the pH value at the beginning of release is not obtained. The release begins, even at a methacrylic acid content of only 10%, at a pH of still 5 to 6. Further, the use of comonomers which reduce the hydrophilicity of the coating, such as butyl or 2-ethylhexyl esters of the acrylic or methacrylic acid, do not afford the object of the present invention, because, in this case as well, the dissolution is only delayed, and the beginning of dissolution is merely shifted towards higher pH values.

In accordance with the present invention, however, it has surprisingly been found that the objective thereof can be obtained by using coatings and/or binders for pharmaceutical forms on the basis of a copolymerizate of ethylenic, unsaturated, radical and polymerizable monomers with a carboxyl group and alkyl esters of such monomers, when the copolymerizate is made up of:

A) about 10 to 25 wt % methacrylic acid,

B) about 40 to 70 wt % methyl acrylate, and

C) about 20 to 40 wt % methyl methacrylate, based on a total copolymerizate weight of 100% by wt.

Preferably, portion A is about 10 to 20 wt % methacrylic acid.

Surprisingly, pharmaceutical forms with coatings of the present composition, which are resistant to gastric juice according to the test in accordance with USP, release essentially no active ingredient at pH 6.8, however, complete release is attained within 60 min at pH 7.5. The advantageous dissolution characteristics of the coatings according to the present invention are evident from FIG. 1. For this, coating films were applied to glass beads in the layer thickness which is customary for pharmaceutical forms and the quantity of polymerizate which dissolved at particular pH values was determined by pH-stat titration with alkali.

In FIG. 1, the dissolution curves for three coating agents according to the invention (B1, B2, B4 corresponding to Embodiment Example Nos. 1, 2, and 4) of the composition (in wt %)

|                    | B1 | B2 | B4 |
|--------------------|----|----|----|
| Methyl acrylate    | 60 | 65 | 70 |
| Methyl methacrylate| 25 | 25 | 20 |
| Methacrylic acid   | 15 | 10 | 10 | are compared with several coating agents (A, V1 to V4) with the compositions (in wt %):

|                     | A  | V1 | V2 | V3 | V4 |
|---------------------|----|----|----|----|----|
| Methyl acrylate     | —  | 50 | —  | —  | —  |
| Ethyl acrylate      | —  | —  | 50 | 65 | 70 |
| Methyl methacrylate | 50 | 20 | 20 | —  | —  |
| Methacrylic acid    | 50 | 30 | 30 | 35 | 30 |

A corresponds to the commercial product, EUDRAGIT L100. The production of V1 is described in Example 3. V2, V3, and V4 were generated in a like manner by emulsion polymerization. The curves for V2, V3, and V4 are almost identical, and are indicated together with V2 in FIG. 1. The advantageously steep course of the curves shifted to higher pH values in the coatings according to the invention, B1, B2, and B4 was not predictable. Above pH 7.5, complete dissolution of the coating is achieved.

Another advantage of the present coating film is the high elasticity and flexibility which is explained by the comparatively low portion of monomer hardening components, such as methyl methacrylate and methacrylic acid. Nevertheless, it is quite surprising that a flexibility which satisfies the practical requirements is achieved only with methyl acrylate which, of all alkyl acrylates, yields the greatest polymerizate hardness as a homopolymerizate. In this way, and in general a softener portion of less than 10 wt % is sufficient, and the softener may even be omitted entirely. This allows the avoidance of disadvantages with regard to technical production which tend to appear when larger quantities of softeners are used.

By virtue of the present invention, a gap in the galenic palette of coating agents with release curves at different pH values is closed. Although coating agents are available which commence release at pH 5.5 to 6.5, coating agents which commence release at pH 7 have been unavailable until the present invention.

Production of the coating agent

The coating agent of the present invention can be produced in a known manner such as by radical emulsion polymerization in the aqueous phase in the presence, preferably of anionic emulsifiers, for example, according to the method described in DE-C 2,135,073.

The monomer components indicated by A, B, and C generally form more than 80 wt %, and preferably 100 wt % of the copolymerizate. The portion which may remain can consist of other acrylic or methacrylic monomers, particularly alkyl esters, such as ethyl acrylate and methacrylate or butyl acrylate and methacrylate. The molecular weight is in the customary range of, for example, 50,000 to 300,000 d.

The copolymerizate can be produced in solution or in emulsion according to conventional methods of radical polymerization in the presence of initiators which form radicals and, optionally, regulators to adjust the molecular weight of the substance. Preferred is emulsion polymerization in an aqueous phase in the presence of water-soluble initiators and, preferably anionic, emulsifiers. The emulsion polymerizate is preferably generated and applied in the form of a 10 to 50 wt %, especially 30 to 40 wt %, aqueous dispersion. For commercial form, a solid content of 30 wt % is preferred. In processing, it is possible to dispense with partial neutralization of the methacrylic acid unit; however, it is possible, for example, in a range up to 5 or 10 mol %, when thickening of the coating dispersion is desired. The weight average value of the latex particle size is generally 40 to 100 nm, preferably 50 to 70 nm, which assures favorable viscosity, below 1000 mPa.s, in commercial processing.

The minimum film formation temperature (MFT according to DIN 53,778) for most of the coatings according to the invention is between 0° and 25° C., so that processing is possible at room temperature without addition of softener. The tensile strength of the film, measured according to DIN 53,455, is generally 50% or more at a content of 10 wt % triethyl citrate, at most.

The softening temperature of the polymerizate film which forms when dry, determined by DSC measurement, preferably is in the range of 40° to 80° C., especially from 45° to 70° C. The temperature stability of the emulsion polymerizates, determined by thermogravimetric analysis $(T_v 0.1)$ is generally above 200° C., usually in the range from 200° to 240° C., which is surprisingly high for copolymers containing carboxyl groups. In this way, it is also possible to process the emulsion polymerizates from the melt. Typical melt viscosities are, for example, 8000 Pa.s at 160° C. for emulsion polymerizates of 60% MA, 20% MMA, 20% MAS 4000 Pa.s at 150° C. for emulsion polymerizates of 60% MA, 25% MMA, 15% MAS (MA=methyl acrylate, MMA=methyl methacrylate, MAS= methacrylic acid, data in wt %).

Processing of the coating agents into pharmaceutical forms

The new coating agents can be processed in a manner which corresponds to that of other known aqueous coating agents on an acrylate base. The most commonly used are the coating pan method and the fluidized bed method. Common additives such as softeners, pigments, fillers, thickening agents, defoaming agents, preservatives, etc., can be incorporated in the commonly used quantities. Coatings can be generated on tablets, coated tablets, granulates, or crystals. The formation of matrix tablets or granulates is also possible. Preferred processing temperatures are in the range of 30° to 60° C. Suitable film thicknesses are 10 to 80 μm.

According to the mechanism of release of the active ingredient, the pH control by means of the coating film can be used not only in the gastrointestinal tract, but also in other body cavities, tissues, the bloodstream, and the habitats of animals and plants in order to cause the release of active ingredients in connection with a change of pH. Examples are coatings which can be introduced into the bloodstream with catheters, implants of veterinary drugs, and vaccines which are mixed with fish food.

As with other aqueous coating agents, layers of multilayer coating systems can also be generated. Likewise, a core, which contains, for example, base or water-sensitive active ingredients, can be provided with an insulating layer of a different coating material such as cellulose ether, cellulose ester, cationic polymethacrylate (such as EUDRAGIT® E100, RL100, RS100, Röhm GmbH), before the coating agent ccording to the invention is applied. Likewise, other coatings, for example, with a flavor-enhancing effect or with appealing color or gloss, can be applied thereafter.

Having described the present invention, reference will now be made to certain examples which are provided solely for purposes of illustration and which are not intended to be limitative.

EXAMPLE 1

297 g of an emulsion polymerizate of 60 parts by wt. methyl acrylate, 25 parts by weight methyl methacrylate, and 15 parts by weight methacrylic acid with 30% dry substance (89 g polymer substance) were diluted by addition of 238 g water. 1000 g round, slightly convex tablet cores of 7 mm diameter, 3.3 mm. height, and 140 mg weight, consisting of lactose (59.2 wt. %), Aerosil 200 (0.5 wt. %), talc (3.0 wt. %), Avicel pH 102 microcrystalline cellulose (30 wt. %), magnesium stearate (0.3 wt. %), Amijel (starch) (5.0 wt. %), as well as methylene blue (2.0 wt. %) as indicator were heated to 30° C. in an onion-shaped coating pan of 25 cm diameter under rotation of 40 rpm with hot air, and the dispersion was sprayed at this temperature with a compressed air pistol at 1 bar pressure. The dispersion was sprayed continuously within 140 min at a spray rate of approximately 4 g dispersion per minute. The coated tablets were then dried for 2 h at 40° C. in the drying cabinet, stored open overnight at room temperature, and their decomposition and dissolution behavior was tested according to USP 711 dissolution/apparatus 2 (paddle). The coated tablets were unchanged in artificial gastric juice for 120 min, and for another 60 min in buffer solution pH 5.0 after pouring off the gastric juice. All tablets decompose within 40 min with buffer solution, pH 6.8.

EXAMPLE 2

Coating Agent B2

Similar to Example 1, 297 g of an emulsion polymerizate of 65 parts by weight methylacrylate, 25 parts by weight methyl methacrylate, and 10 parts by weight methacrylic acid with 30% dry content, corresponding to 89 g polymer substance, were mixed with 22.3 g talc and diluted with 238 g water. The processing was done as in Example 1 under the conditions described there. The spray rate was 4.5 g/min and thereby, a spray time of 124 min resulted. The coated tablets were then dried as in Example 1 and tested. They were resistant to gastric juice for 2 h, did not dissolve in pH 5.0 and 6.8 buffer solutions, over 60 min in each case, and decomposed in pH 7.5 buffer solutions within 50 min after dissolution of the methylene blue dye.

EXAMPLE 3

Comparison Polymerizate V1

As described in Example 1, an emulsion polymerizate of 50 parts by weight methylacrylate, 20 parts by weight methyl methacrylate, and 30 parts by weight methacrylic acid was processed with the addition of 8.9 g triethyl citrate as a softener. The coated tablets were resistant to gastric juice for 2 h, after 60 min were not changed in pH 5.0 buffer solution, and decomposed in pH 6.5 buffer solution within 1 h.

EXAMPLE 4

Coating Agent B4

1 kg spherical particles with a diameter of 0.8–1.2 mm, containing 4.4 wt % bisacodyl as active ingredient, were sprayed in a fluidized bed device, GPC of the Glatt GmbH Company, D-79589 Binzen, under constant churning with a mixture of 417 g of a 30% emulsion polymerizate of 70 parts by weight methacrylate, 20 parts by weight methyl methacrylate, and 10 parts by weight methacrylic acid and an emulsion of 3.8 g glycerin monostearate in 224 g water. The spray rate was 10 g/min, whereby the spray dispersion was transported continuously to the spray nozzle of the fluidized bed device by means of a hose pump. The coated pellets were tested according to USP XXII apparatus 2 (paddle) for gastric juice resistance and dissolution rate in pH 6.8 buffer solution. The release of bisacodyl from the pellets which did not decompose in gastric juice was less than 3% after 2 h. After changing the test liquid to 6.8 buffer solution, the pellets gradually decomposed and released the contained active ingredient to over 99% within 45 min.

Having described the present invention, it will be apparent to one of ordinary skill in the art that many changes and modifications may be made to the above-described embodiments without departing from the spirit or the scope of the present invention.

What is claimed as new and desired to be secured by Letters Patent of the United States is:

1. A composition, comprising:
   (a) a pharmaceutical compound; and
   (b) a copolymer comprising:
      A) about 10–25 wt. % methacrylic acid,
      B) about 40–70 wt. % methyl acrylate, and
      C) about 20–40 wt. % methyl methacrylate, based on a total copolymer weight of 100 wt. %.

2. The composition of claim 1, wherein said copolymer comprises 80 wt. % of components A, B and C.

3. The composition of claim 2, wherein said copolymer further comprises a monomer selected from the group consisting of ethyl acrylate, ethyl methacrylate, butyl acrylate and butyl methacrylate.

4. The composition of claim 1, wherein said copolymer has a molecular weight of 50,000–300,000 daltons.

5. The composition of claim 1, wherein said copolymer comprises 10–20 wt. % methacrylic acid.

6. The composition of claim 1, wherein said copolymer has a minimum film formation temperature of about 0°–25° C.

7. The composition of claim 1, wherein said copolymer has a softening temperature of from 40°–80° C.

8. The composition of claim 1, wherein said copolymer is a coating covering said pharmaceutical compound.

9. The composition of claim 8, wherein said coating has a thickness of about 10–80 microns.

10. The composition of claim 1, wherein said copolymer is a binder for said pharmaceutical compound.

11. The composition of claim 1, wherein said methacrylic acid is 5–10 mol % neutralized.

12. The composition of claim 1, wherein said composition comprises a tablet, granulate or crystal.

13. The composition of claim 12, wherein said tablet is a coated tablet or matrix tablet.

14. The composition of claim 1, further comprising a flavor-enhancing or coloring coating.

15. The composition of claim 8, wherein said pharmaceutical compound is released from said coating only at a pH of about 6.5 or higher.

16. The composition of claim 15, wherein said pharmaceutical compound is completely released from said coating at a pH of 6.8–7.5.

17. The composition of claim 1, wherein said pharmaceutical compound is a drug or vaccine.

18. A method of forming a pharmaceutical composition, comprising the steps of:
   (1) coating or binding a pharmaceutical compound with a copolymer comprising:
      A) about 10–25 wt. % methacrylic acid,
      B) about 40–70 wt. % methyl acrylate, and
      C) about 20–40 wt. % methyl methacrylate, based on a total copolymer weight of 100 wt. %.

19. The method of claim 18, wherein said coating step comprises coating said pharmaceutical compound with an aqueous latex of said copolymer having a particle size of about 40–100 nm.

20. The method of claim 18, wherein said pharmaceutical composition comprises a tablet, granule or crystal.

* * * * *